United States Patent
Schlitt et al.

(10) Patent No.: US 10,953,152 B2
(45) Date of Patent: Mar. 23, 2021

(54) PIERCING PART FOR A MEDICAL INFUSION SYSTEM, DRIP CHAMBER AND INFUSION SYSTEM

(71) Applicant: B. Braun Melsungen AG, Melsungen (DE)

(72) Inventors: Christof Schlitt, Obergrenzebach (DE); Manfred Lutz, Spangenberg (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 344 days.

(21) Appl. No.: 15/884,806

(22) Filed: Jan. 31, 2018

(65) Prior Publication Data

US 2018/0221572 A1   Aug. 9, 2018

(30) Foreign Application Priority Data

Feb. 3, 2017   (DE) .................... 10 2017 201 755.4

(51) Int. Cl.
*A61M 5/162* (2006.01)
*A61M 5/14* (2006.01)
*A61J 1/20* (2006.01)

(52) U.S. Cl.
CPC ............ *A61M 5/162* (2013.01); *A61J 1/2072* (2015.05); *A61M 5/14* (2013.01); *A61M 5/1411* (2013.01); *A61M 2202/04* (2013.01)

(58) Field of Classification Search
CPC ...... A61M 5/14; A61M 5/1411; A61M 5/162; A61J 1/2072
USPC ................................. 604/244, 272, 273, 274
See application file for complete search history.

(56) References Cited

U.S. PATENT DOCUMENTS

| | | | |
|---|---|---|---|
| 2006/0135917 A1* | 6/2006 | Reihl | A61B 5/14528 604/272 |
| 2009/0326485 A1* | 12/2009 | Carlyon | A61J 1/2096 604/272 |
| 2010/0312220 A1 | 12/2010 | Kalitzki | |
| 2011/0275988 A1* | 11/2011 | Davis | A61M 39/20 604/82 |
| 2013/0218102 A1* | 8/2013 | Iwase | A61M 5/00 604/272 |

(Continued)

FOREIGN PATENT DOCUMENTS

| | | |
|---|---|---|
| DE | 3901068 A1 | 8/1989 |
| DE | 19748497 A1 | 5/1999 |
| DE | 102007061346 A1 | 6/2009 |

(Continued)

OTHER PUBLICATIONS

Extended European Search Report for European Application No, 18 153 124.5, dated Jul. 4, 2018, with partial translation, 11 pages.

(Continued)

*Primary Examiner* — Brandy S Lee
*Assistant Examiner* — Nidah M Hussain

(57) ABSTRACT

A piercing part for a medical infusion system includes a piercing mandrel through which at least one channel extends and which has a mandrel tip whose first jacket surface part is tapered, relative to a central longitudinal axis, towards a front end. An opposite second jacket surface part has an inclined cutting face interrupted towards the front end. The piercing part can be used for medical transfusion and infusion appliances.

13 Claims, 3 Drawing Sheets

(56) References Cited

U.S. PATENT DOCUMENTS

Figure 1:
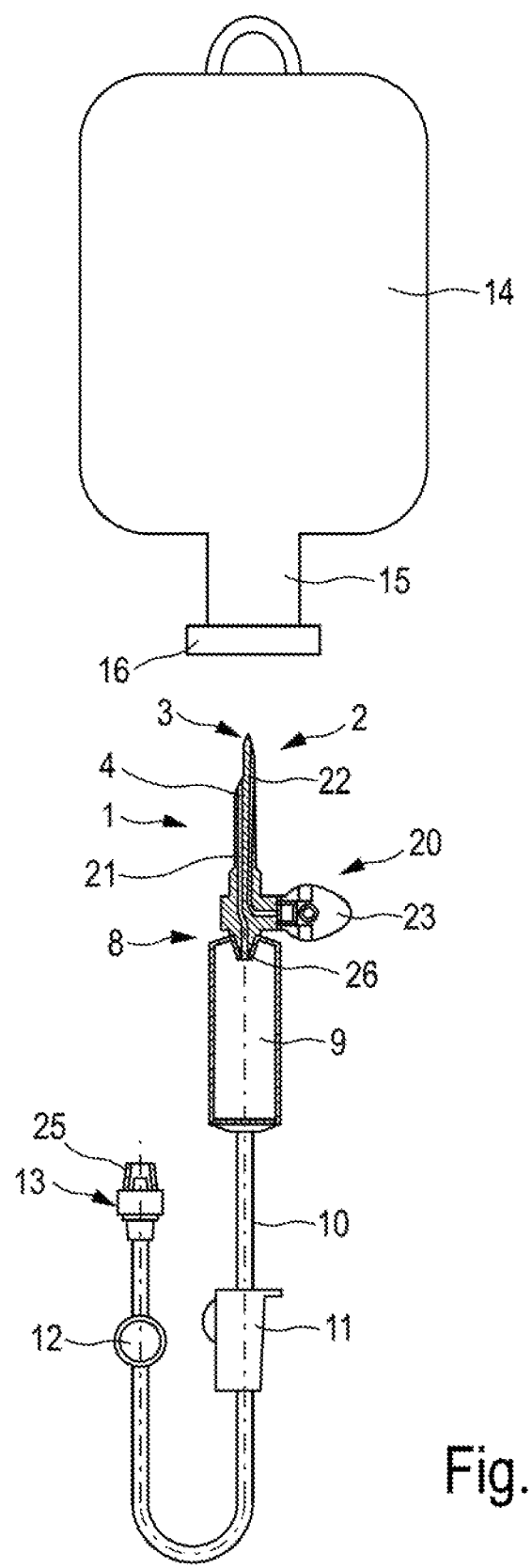

2013/0331811 A1* 12/2013 Butterfield ............ A61M 5/142
                                                             604/500
2014/0014210 A1   1/2014 Cederschiold

FOREIGN PATENT DOCUMENTS

WO      02064438 A2   8/2002
WO   2010029371 A2   3/2010

OTHER PUBLICATIONS

German Search Report for German Application No. 10 2017 201 755.4, dated Dec. 5, 2017 with partial translation, 9 pages.

* cited by examiner

PIERCING PART FOR A MEDICAL INFUSION SYSTEM, DRIP CHAMBER AND INFUSION SYSTEM

RELATED APPLICATION(S)

This application claims the benefit of priority under 35 U.S.C. § 119 of German Application No. 10 2017 201 755.4, filed Feb. 3, 2017, the contents of which is incorporated by reference herein in its entirety.

FIELD

The invention relates to a piercing part for a medical infusion system, with a piercing mandrel through which at least one channel extends and which has a mandrel tip whose first jacket surface part is tapered, relative to a central longitudinal axis, towards a front end. The invention moreover relates to a drip chamber and an infusion system with a corresponding piercing part.

BACKGROUND

A piercing part of this kind for infusion appliances is known from the laid-open application DE 197 48 497 A1. The known infusion appliance has a piercing mandrel which is integrally formed on a drip chamber. The piercing mandrel contains a liquid channel and an air channel and has a mandrel tip tapering to a point.

SUMMARY

An object of this disclosure is to make available a piercing part, a drip chamber and an infusion system of the type mentioned at the outset, which pose a lower risk of potential injury and yet require application of a relatively low force in order to pierce a liquid container.

For the piercing part, this object is achieved by the fact that an opposite second jacket surface part has an inclined cutting face interrupted towards the front end. The invention relates in particular to infusion systems that can be operated by gravity. The piercing part has a housing which is preferably designed as part of a drip chamber. By virtue of the solution according to the invention, a mandrel tip can be created which poses less risk of injury. At the same time, pierceable seals of liquid containers can be punctured by application of relatively low force. The first and second jacket surface parts are to be understood as outer contours of the mandrel tip of the piercing mandrel that lie opposite each other.

In one embodiment of the invention, the tapered first jacket surface part and the opposite second jacket surface part are inclined in mutually opposite directions towards the front end. A geometry is thus advantageously created in which the piercing part widens in the direction of the drip chamber, such that a portion opposite the drip chamber has a smaller cross section. The geometry is configured in the manner of a two-sided blade since both jacket surface parts run obliquely, in mutually opposite directions, towards a front end of the mandrel tip.

In a further embodiment of the invention, the first jacket surface part is tapered geometrically continuously. The tapering thus has no steps, shoulders or edges. This allows the piercing part to pierce a pierceable seal or a closure plug of a liquid container with relatively constant resistance.

In a further embodiment of the invention, the first jacket surface part has a curved or arched contour. The curve or arch is preferably convex or bulged.

In a further embodiment of the invention, the cutting face is interrupted by a transversely extending edge and is plane towards the front end. This results in a constant cutting force or piercing force along the length of the cutting face.

In a further embodiment of the invention, the cutting face is inclined, relative to a radial plane of the central longitudinal axis of the piercing mandrel, in an angle range of between 30° and 70°, preferably of between 45° and 60°. In this angle range, it is advantageously possible to achieve a good piercing behavior of the piercing mandrel, such that the piercing mandrel, with relatively low force applied by an operator, is able to pierce a pierceable seal or a closure plug of a liquid container.

In a further embodiment of the invention, the second jacket surface part, away from the front end as seen in the longitudinal direction, merges into a contour region in which a liquid channel opens out. The contour region is advantageously configured in such a way that, in a state of use of the piercing part in which the piercing part is connected to the liquid container, a liquid can flow from the liquid container into the liquid channel. The contour region has a mouth aperture of the liquid channel.

In a further embodiment of the invention, an opening of a ventilation channel is provided in the first jacket surface part, which opening is provided opposite the cutting face of the second jacket surface part. This minimizes the risk of mixing together of air flowing into the liquid container and of liquid flowing out of the liquid container. Moreover, the ventilation channel lies closer to the mandrel tip of the piercing part and thus in a state of use higher than the admission opening of the liquid channel, such that the danger of air and liquid mixing together is further minimized.

In a further embodiment of the invention, a transition region extending between the transversely extending edge and the contour region is configured as a plane transition face extending parallel to the central longitudinal axis. In this region, the cross section of the piercing part changes relatively little, and a force for piercing the liquid container remains relatively constant.

BRIEF DESCRIPTION OF THE DRAWING FIGURES

Further advantages and features of this disclosure will become clear from the following description of a preferred but non-limiting exemplary embodiment which is shown in the drawings.

Figure 2:
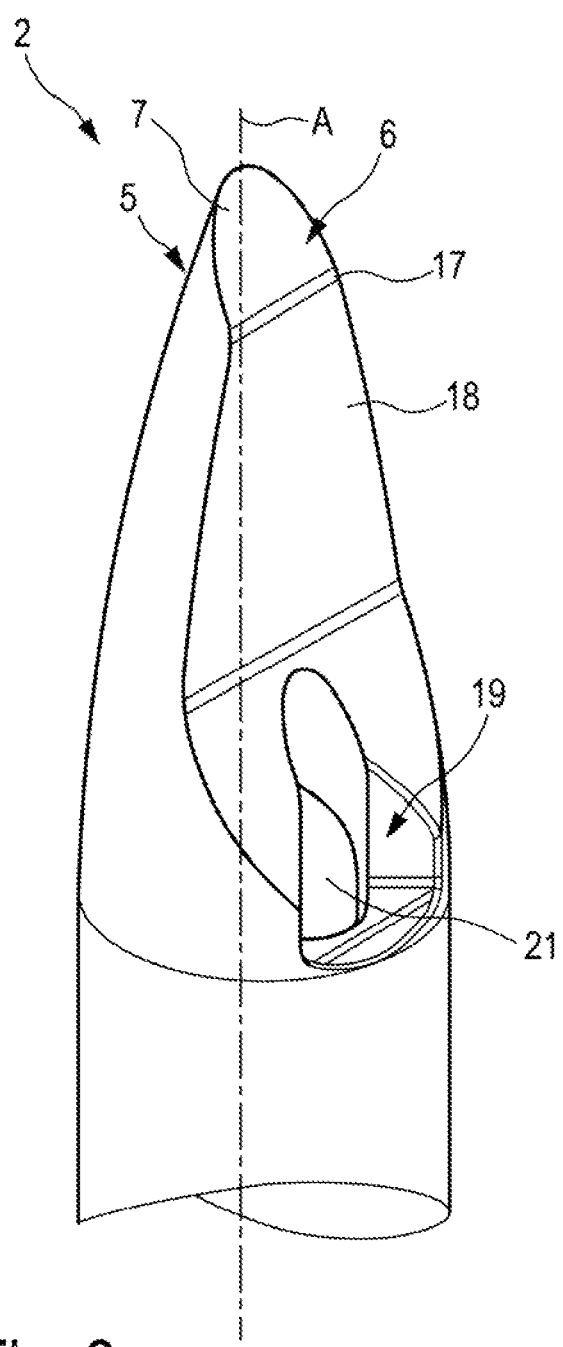
Figure 3:
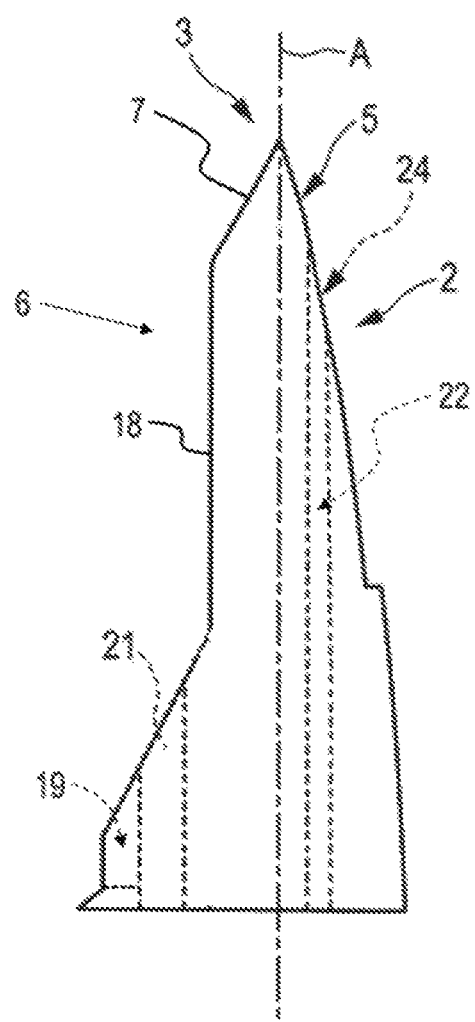
Figure 4:
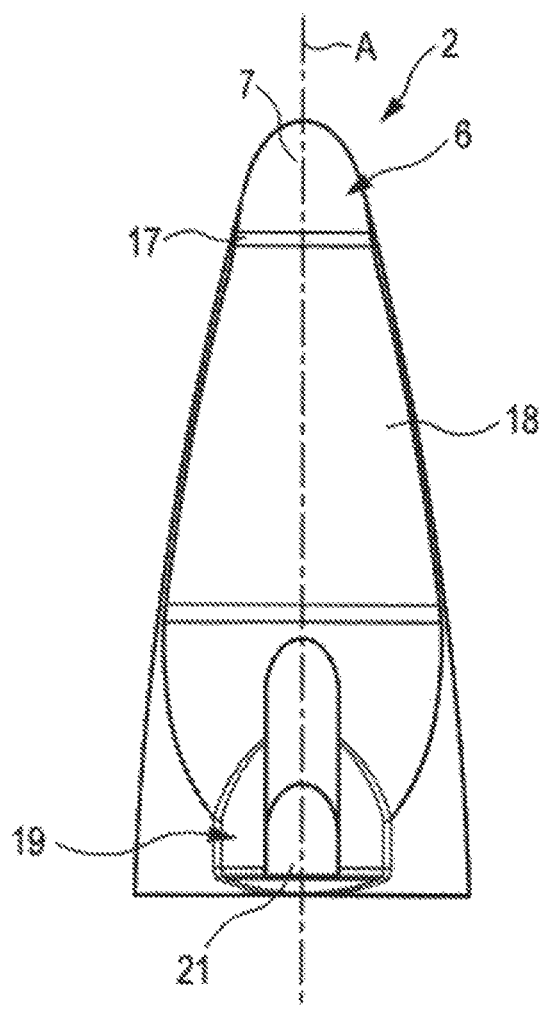

FIG. 1 shows a sectional view of an infusion system according to an embodiment of the invention with a drip chamber according to an embodiment of the invention and a piercing part according to an embodiment of the invention, FIG. 2 shows an isometric view of a piercing mandrel of the piercing part shown in FIG. 1, FIG. 3 shows a side view of the piercing mandrel shown in FIG. 2, and FIG. 4 shows a front view of the piercing part shown in FIGS. 2 and 3.

DETAILED DESCRIPTION

A medical infusion system serves to transfer a liquid from a liquid container 14 to a patient. The liquid is conveyed out of the liquid container 14 and conveyed through the infusion system to the patient. According to FIG. 1, the infusion system has a piercing part 1. In an upper region in the viewing plane of FIG. 1, the piercing part 1 has a piercing mandrel 2 with a mandrel tip 3 which, in a viewing plane of FIG. 1, points upwards, i.e. towards the liquid container 14. In a lower region, i.e. in a region directed towards the mandrel tip 3 of the piercing part 1, the liquid container 14 is provided with a pierceable portion 15, which has a pierceable seal 16 in the form of a closure plug. In a delivery state of the liquid container 14, the pierceable portion 15 is closed in a liquid-tight manner by means of the pierceable seal 16.

In the exemplary embodiment shown according to FIG. 1, the infusion system comprises the piercing part 1, which has a housing 8 that is part of a drip chamber 9. The piercing mandrel 2 is formed integrally on the drip chamber 9. A drip tube 26, which is an integral constituent of the piercing part 1, opens into the drip chamber 9. The piercing mandrel 2 runs out into the mandrel tip 3. The piercing part 1 has an inner channel 4, which is here designed as a liquid channel 21. Furthermore, the infusion system comprises the drip chamber 9, which adjoins the piercing mandrel 2 downstream in a direction of flow of the infusion system, a hose line 10, which adjoins the drip chamber 9 downstream and which has a flow regulator 11 and an injection port 12, and an attachment piece 13 for attaching to an interface to the patient, which attachment piece 13 is closed with a releasable cap 25.

The infusion system shown is operated by gravity, such that the liquid container is held hanging down and the piercing mandrel 3 pierces it vertically from below. The drip chamber is also oriented vertically in its functional position.

In a delivery state of the liquid container 14, the pierceable portion 15 of the liquid container 14 is closed by the pierceable seal 16 and has to be penetrated by the mandrel tip 3 of the piercing part 1 before the infusion system is put into operation, in order to permit a transfer of liquid from the liquid container 14 into the infusion device. In a delivery state of the infusion system, the piercing part 1 is covered by a protective cap (not shown) in order to protect an operator from injury on the mandrel tip 3 and in order to protect the piercing part 1 from contamination.

In the functional position (not shown), the liquid container 14 is connected to the infusion system. The protective cap (not shown) of the piercing part 1 is removed and the pierceable seal 16 of the pierceable portion 15 is penetrated by the mandrel tip 3 and by the piercing mandrel 2 of the piercing part 1, thereby permitting a transfer of liquid between the liquid container 14 and the hose line 10 and the patient.

According to FIG. 3, the piercing part 1 has a central longitudinal axis A. In a viewing plane of FIG. 3, a first jacket surface part 5 is arranged to the right of the central longitudinal axis A in an upper region. The first jacket surface part 5 is tapered geometrically continuously. In the exemplary embodiment shown, the first jacket surface part 5 describes a gently curved contour. To the left of the central longitudinal axis A, the second jacket surface part 6 is arranged opposite the first jacket surface part 5. Both jacket surface parts 5, 6 are inclined in mutually opposite directions towards a front end, i.e. an upper end of the piercing mandrel 2. An upper region of the first jacket surface part 5 forms a mandrel tip 3 with an upper region of the second jacket surface part 6.

According to FIGS. 2 and 4, the second jacket surface part 6 of the mandrel tip 3 defines a cutting face 7, which is interrupted by a transversely extending edge 17 and is plane towards a front end of the piercing mandrel 2, i.e. an upper end. In the exemplary embodiment shown, the cutting face 7 is inclined relative to a radial plane of the central longitudinal axis A of the piercing part 1 by an angle of ca. 45°.

In a lower region of the piercing part 1, the second jacket surface part 6 merges into a contour region 19 in which a liquid channel 21 opens out.

According to FIG. 2, a transition region 18, configured as a plane transition face extending parallel to the central longitudinal axis A, is provided between the transversely extending edge 17, which forms the lower termination of the cutting face 7, and the contour region 19.

According to FIG. 1, a ventilation device 20 is arranged in a region between the piercing mandrel 2 and the drip chamber 9. The ventilation device 20 has an outer ventilation valve 23, which can connect an inner ventilation channel 22 to the atmosphere. The liquid channel 21 and the ventilation channel 22 extend at least substantially parallel to each other in an interior of the piercing mandrel 2, wherein the ventilation channel 22 in the piercing mandrel 2 opens out above the liquid channel 21 in order to ensure ventilation of the liquid container 14 but to rule out any admixture of air in the liquid channel 21. In a region of the piercing mandrel 2 directed towards the drip chamber 9, the ventilation channel 22 extends, at right angles to the liquid channel 21, towards the ventilation valve 23.

According to FIG. 3, the piercing part 1 has, on the first jacket surface part 5, an opening 24 of the ventilation channel 22, which opening 24 is arranged opposite the liquid channel 21 of the second jacket surface part 6.

In order to create a liquid connection between the liquid container 14 and the infusion system, a sterile package (not shown), in which the infusion system is packed in the delivery state, is opened by the operator and the infusion system is removed from the package. In this state, the drip chamber 9 is connected upstream to the piercing part 1 and downstream to the hose line 10. The ventilation device 20 is secured laterally on the piercing device 1. At a distance from the drip chamber 9, the flow regulator 11 surrounds a region of the hose line 10. The injection port 12 is arranged at a distance downstream from the flow regulator. In other embodiments of the infusion system, such an injection port 12 is not present. Downstream from the injection port 12, the attachment piece 13 is mounted on the hose line and closed by the releasable cap.

The protective cap (not shown) of the piercing mandrel 2 is connected releasably to the piercing part 1 and covers the piercing mandrel 2. The protective cap (not shown) is removed by the operator, and the mandrel tip 3 of the piercing part 1 is inserted into the pierceable seal 16 of the pierceable portion 15 of the liquid container 14. The cutting face 7 formed by the upper portions of the first and second jacket surface part 5, 6 cuts into the pierceable seal 16. The transition region 18 adjoining the mandrel tip 3 is then pushed through the pierceable seal 16, and a lower region of the piercing part 1 is pushed through the pierceable seal 16. A liquid connection is thus produced between the liquid container 14 and the infusion system, and the liquid from the liquid container 14 can flow by gravity via the contour region 19 and through a mouth of the liquid channel 21 into the drip chamber 9. The drip chamber 9 permits observation of the falling drips and is for this purpose formed from a transparent material. The drip chamber 9 has the inner drip tube 26 which protrudes into the drip chamber 9 and through which the liquid enters the drip chamber 9. The inner cross section of the drip tube 26 represents a continuation of the liquid channel 21. Through the drip chamber 9, the liquid passes to the hose line 10 and reaches the patient via the attachment piece 13. The hose line 10 is formed from a flexible and transparent material in order to allow the operator to discern a flow of liquid or air. The attachment piece 13 has an outer cone for connecting to the interface to the patient. In order to permit a pressure compensation in the liquid container 14 as liquid flows out, the liquid container 14 is ventilated via the ventilation device 20 during the use of the infusion system. The ventilation valve 23 opens for this purpose, such that air can flow through the ventilation channel 22 into the liquid container 14. In order to avoid contamination of the liquid, the ventilation device has an air filter (not shown). The flow velocity can also be varied by means of the flow regulator 11. For this purpose, a cross section of the hose 10 is modified by the flow regulator 11, particularly in the form of a roller clamp, such that a through-flow volume of the liquid is reduced. Moreover, the cross section of the hose line 10 can be reduced to such an extent that a flow through the hose line 10 is completely suppressed. By way of the injection port 12, further liquids may if necessary be admixed to the liquid from the liquid container 14. The injection port 12 is for this purpose designed to be self-closing.

What is claimed:

1. A piercing part for a medical infusion system, the piercing part comprising a piercing mandrel through which at least one channel extends, the piercing mandrel comprising a mandrel tip having:
    a first jacket surface part having a curved or arched contour that is tapered in a first direction relative to a central longitudinal axis toward a front end;
    an opposite second jacket surface part comprising an inclined cutting face that is inclined in a direction opposing the first direction relative to the central longitudinal axis, wherein the inclined cutting face intersects the tapered first jacket surface part at the front end, such that the front end has a curved or arched edge; and
    a transition region interrupting the second jacket surface part behind the inclined cutting face and extending parallel to the central longitudinal axis.

2. The piercing part according to claim 1, wherein the first jacket surface part and the second jacket surface part are inclined in mutually opposite directions towards the front end.

3. The piercing part according to claim 1, wherein the first jacket surface part is tapered geometrically continuously.

4. The piercing part according to claim 1, wherein the transition region interrupts the cutting face at a transversely extending edge and is planar towards the front end.

5. The piercing part according to claim 4, wherein the cutting face is inclined, relative to a radial plane of the central longitudinal axis of the piercing mandrel, at an angle range of between 30° and 70°.

6. The piercing part according to claim 4, wherein the second jacket surface part, away from the front end as seen in a longitudinal direction, merges into a contour region in which a liquid channel opens out.

7. The piercing part according to claim 1, wherein an opening of a ventilation channel is provided in the first jacket surface part, the opening being provided opposite the cutting face of the second jacket surface part.

8. The piercing part according to claim 6, wherein the transition region extends between the transversely extending edge and the contour region.

9. A drip chamber for a medical infusion system comprising a piercing part according to claim 1.

10. A medical infusion system comprising a drip chamber according to claim 9.

11. A medical infusion system comprising a piercing part according to claim 1.

12. The piercing part according to claim 1, wherein the mandrel tip further comprises:
    a contour region below the transition region and comprising surfaces extending inwardly toward the central longitudinal axis from the second jacket surface to a liquid channel.

13. A piercing part for a medical infusion system, the piercing part comprising:
    a piercing mandrel through which at least one channel extends, the piercing mandrel having a mandrel tip comprising a curved distal edge, the curved distal edge comprising a distal-most point of the mandrel tip, the mandrel tip comprising:
    a first jacket surface part having a curved or arched contour that is tapered in a first direction relative to a central longitudinal axis;
    an opposite second jacket surface part comprising an inclined cutting face that is inclined in a direction opposing the first direction relative to the central longitudinal axis, wherein the inclined cutting face intersects the tapered first jacket surface part at the distal-most point of the curved distal edge; and
    a transition region interrupting the second jacket surface part behind the inclined cutting face and extending parallel to the central longitudinal axis.

* * * * *